United States Patent [19]
Hall

[11] Patent Number: 5,490,916
[45] Date of Patent: Feb. 13, 1996

[54] CAPILLARY REFERENCE HALF-CELL

[75] Inventor: Stephen H. Hall, Kennewick, Wash.

[73] Assignee: Battelle Memorial Institute, Richland, Wash.

[21] Appl. No.: 290,764

[22] PCT Filed: Apr. 14, 1993

[86] PCT No.: PCT/US93/03568

§ 371 Date: Aug. 12, 1994

§ 102(e) Date: Aug. 12, 1994

[87] PCT Pub. No.: WO94/06003

PCT Pub. Date: Mar. 17, 1994

[51] Int. Cl.$^6$ .................................................. G01N 27/26
[52] U.S. Cl. .................. 205/775; 204/435; 205/794.5
[58] Field of Search .................................. 204/435, 153.1

[56] References Cited

U.S. PATENT DOCUMENTS

| | | | |
|---|---|---|---|
| 2,289,589 | 7/1942 | Pomeroy | 204/435 |
| 3,455,793 | 7/1969 | Watanabe et al. | 204/435 |
| 3,463,717 | 8/1969 | Koopman et al. | 204/435 |
| 3,705,089 | 12/1972 | Grubb | 204/435 |
| 4,929,426 | 5/1990 | Bodai et al. | 204/435 |

OTHER PUBLICATIONS

Hack One Electrode System Manual, 1988 pp. I, 1, 3, 16, 22–26.

Primary Examiner—Bruce F. Bell
Attorney, Agent, or Firm—Paul W. Zimmerman

[57] ABSTRACT

The present invention is a reference half-cell electrode wherein intermingling of test fluid with reference fluid does not affect the performance of the reference half-cell over a long time. This intermingling reference half-cell may be used as a single or double junction submersible or surface reference electrode. The intermingling reference half-cell relies on a capillary tube having a first end open to reference fluid and a second end open to test fluid wherein the small diameter of the capillary tube limits free motion of fluid within the capillary to diffusion. The electrode is placed near the first end of the capillary in contact with the reference fluid. The method of operation of the present invention begins with filling the capillary tube with a reference solution. After closing the first end of the capillary, the capillary tube may be fully submerged or partially submerged with the second open end inserted into test fluid. Since the electrode is placed near the first end of the capillary, and since the test fluid may intermingle with the reference fluid through the second open end only by diffusion, this intermingling capillary reference half-cell provides a stable voltage potential for long time periods.

18 Claims, 6 Drawing Sheets

CAPILLARY REFERENCE HALF-CELL

This invention was made with Government support under Contract DE-AC06-76RLO 1830 awarded by the U.S. Department of Energy. The Government has certain rights in the invention.

FIELD OF THE INVENTION

The present invention relates generally to a method and apparatus for providing a reference half-cell or more specifically to a capillary type reference half-cell having a liquid reference solution constrained from free flow volume discharge.

BACKGROUND OF THE INVENTION

Investigation of the chemistry of natural waters including but not limited to underground aquifers, and above ground lakes is usually accomplished by taking water samples and analyzing the samples in a laboratory. Many chemical species are detected and measured for various purposes. For example, waste water discharge may be monitored for the presence of hazardous chemicals including but not limited to inorganic cations and anions, for example, sulfur compounds and metal compounds, and organic compounds. Another application is the detection and quantification of chemical tracers which are used for determining flow patterns. Chemical tracers include but are not limited to bromides, chlorides, sulfides, and pH. In addition, chemical analyses are routinely performed for chemical process flow stream monitoring of processes including but not limited to winemaking, electroplating, hydrometallurgy, papermaking, chemical manufacture, and many other industrial processes.

Analysis for determining the presence and amount of particular chemical species may be carried out using an electrochemical cell wherein the voltage potential is related to a difference in chemical concentration between a known reference solution and the unknown sample test solution. The classic electrochemical cell is two beakers having solutions of differing concentrations or compositions with a salt bridge in contact with both solutions and electrodes in each solution which are connected to a voltmeter. The classical electrochemical cell has the attributes of (1) physical isolation of the two solutions, and (2) electrical communication (via a salt bridge) between the two solutions, and is useable in a laboratory setting, but is inconvenient for field applications, especially submerged in-situ measurement applications.

Various methods and devices relying on the physical principles of the classic electrochemical cell have been used in field applications. In field applications, the beakers of the classic cell are replaced with a sensing half-cell and a reference half-cell which are placed in a test solution and connected by a voltmeter. Reference half-cells for field applications have the same two attributes of solution isolation with electrical communication as the classical electrochemical cell. Isolation of the solutions is fundamentally necessary because intermingling of solutions would change the electrochemical potential. Reference half-cells for field applications, grouped according to how solution intermingling is prevented, tend to be of two main types; non-flowing and flowing, wherein the reference solution either flows from the half-cell or it remains within the half-cell.

Electrochemical reference half-cells of the non-flowing type include the liquid filled classical cell and a gel filled submersible cell, for example, a Model 13-620-259 gel-filled calomel reference half-cell, manufactured by Fisher Scientific Company, Pittsburgh, Pa. In gel-filled cells, an amount of reference solution is placed within a vessel and remains within the vessel, hence the solution is non-flowing. In the classic cell, the connection between the non-flowing reference solution and the test solution is a salt bridge, and in the submersible cell, it is a virtually non-porous solid which closes one end of the vessel containing the reference solution. Hence, as in the classical cell, the gel-filled cell reference solution gel is physically prevented from intermingling with test solution yet is in electrical contact through the virtually non-porous solid. The virtually non-porous solid forms an electrical junction. Ideally, it is desirable to minimize the effect of such a junction on the operation of the half-cell. The effect of the junction is minimized by making the virtually non-porous solid as short or thin as practical. The classic cell cannot be submerged since the open beakers would not prevent entry of fluid or liquid in which the cell is submerged, thereby spoiling the concentration of the reference solution liquid within the cell. The submersible cell is completely filled with an incompressible gel so that when the cell is submerged, fluid or liquid cannot enter the cell. However, the virtually non-porous solid causes variable junction potential and an electrically noisy signal thereby limiting the accuracy of measurements made using this device.

Electrochemical reference half-cells of the flowing type include, for example, a Model 13-620-216 Ag/AgCl reference half-cell, manufactured by Fisher Scientific Company, Pittsburgh, Pa. Half-cells of this type require reference solution to flow or leak into the test solution. The flow is controlled by a porous or fritted opening that allows reference fluid to flow from the vessel. As in the gel-filled half-cell, the frit creates an electrical junction. The behavior of the electrical junction is stabilized by allowing the reference solution fluid to flow from the vessel into the test solution fluid. Therefore, the flowing half-cell maintains a more constant voltage potential compared to the non-flowing gel-filled half-cell. However, with a flowing half-cell, one has a tradeoff between making measurements only during the time (often limited to several hours) that there is sufficient reference solution fluid in the half-cell, or periodically adding sufficient reference solution fluid to allow longer term measurements. Moreover, the flowing half-cell is not submersible because the flow would cease or reverse thereby diluting the reference solution fluid with test solution fluid within the vessel.

A flowing, capillary type half-cell reduces the amount of reference solution liquid needed to provide a stable, constant voltage potential, as compared to a flowing non-capillary half-cell. A flowing, capillary type, for example, a Hach One model 44250 single junction reference half-cell, manufactured by Hach Chemical Co., Loveland, Colo., is fundamentally different from the non-capillary half-cells in that the end of the capillary is open rather than closed with a non-porous material or frit. Nevertheless, an electrical junction is formed by the interface between the two fluids, specifically liquids. This liquid junction is ideal because there is no plug material thereby producing a very stable signal. An electrode is mounted within the capillary and near the liquid junction close to the open end of the capillary. The reference solution liquid is in a syringe connected to the capillary tube. The capillary reduces the volume of reference solution liquid needed to flow into the test solution liquid and thereby maintain a stable voltage potential. In operation, the syringe is depressed a small amount to discharge reference solution liquid from the open end of the capillary prior to making a measurement.

Since the capillary is open, intermingling of the test solution liquid and the reference solution liquid within the capillary will eventually change the concentration of reference solution liquid at the electrode and require an additional discharge of reference fluid. Although this capillary reference half-cell has the advantage of stability, and it is convenient for benchtop measurements because the reference solution liquid is easily replenished, the ease of replenishment does not permit submerged operation and the proximity of the electrode to the open end does not permit prolonged operation because it requires frequent flow of reference solution liquid.

There is yet another reference half-cell described in U.S. Pat. No. 3,705,089 to Grubb that is gel-filled but open ended. However, the gel that is in direct contact with test solution liquid changes as a result of that contact thereby affecting the electrical potential of the half-cell. Grubb identifies the need to "renew" the gel/test solution liquid junction. In this case, the liquid junction is formed by an interface between the reference solution gel and a test solution liquid wherein the interface is distinct and the reference solution, being a gel, does not flow through the tube for operation of the half-cell. Grubb does not describe how the interface or junction degrades, but clearly indicates that renewal is necessary. Renewal of the junction is accomplished by cutting off a small segment of the gel-filled tube at its open end. Since cutting and removing material is, in general terms, a bulk volume discharge, this half-cell may be considered of the "flowing" type. A disadvantage of this half-cell is the need to renew the junction by cutting thereby limiting both the time between measurements and the remoteness of measurements.

All of the reference half-cells discussed and described above are of the single junction type. In some applications, it is desirable to have a double junction reference half-cell. The flowing type cell can be used as a double junction cell by placing a first vessel having a fritted opening within a second vessel having a fritted or ground glass opening. The solution fluid in the second vessel is different from the reference solution fluid in the first vessel. The main advantage of a double junction half-cell is that the solution fluid in the outer vessel physically and chemically isolates the reference solution from the test solution fluid while maintaining electrical communication between the two solution fluids.

It is apparent from the foregoing discussion that prior to the present invention, there was no known apparatus or method providing a half-cell that did not require renewal of the liquid junction for stable electrochemical measurements. Further, before the present invention, there was no known submersible capillary half-cell, nor was there a double junction submersible capillary half-cell. It would be advantageous to have a double junction submersible reference half-cell for detecting and measuring concentrations of chemical species. Those skilled in the art would further find advantages in a reference half-cell either single or double junction that did not require replenishment of a reference solution fluid yet provided a stable voltage potential over a long time period of at least several weeks. The present invention further provides ability to make in-situ chemical measurements in real time at a substantially lower cost than by laboratory analysis of field samples.

SUMMARY OF THE INVENTION

The present invention is a capillary reference half-cell allowing intermingling of test solution liquid within reference solution liquid within the capillary. The reference half-cell of the present invention may be used as a single or double junction submersible or surface reference half-cell. The intermingling reference half-cell relies on a capillary tube having a first end open to reference fluid and a second end open to test solution liquid wherein the small diameter of the capillary tube limits free motion of fluid within the capillary to diffusion. An electrode is placed near the first end of the capillary in contact with the reference solution liquid. The length of the capillary determines the service life of the intermingling reference half-cell.

The method of operation of the present invention begins with filling the capillary with a reference solution liquid. After closing the first end of the capillary, the capillary may be fully submerged or partially submerged with the second open end inserted into test solution liquid. Since the electrode is placed near the first end of the capillary, and since the test solution liquid may enter the second open end only by diffusion, this intermingling reference half-cell provides a stable voltage potential for extended time periods, up to several weeks. The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

DESCRIPTION OF THE PREFERRED EMBODIMENT(S)

Figure 1:
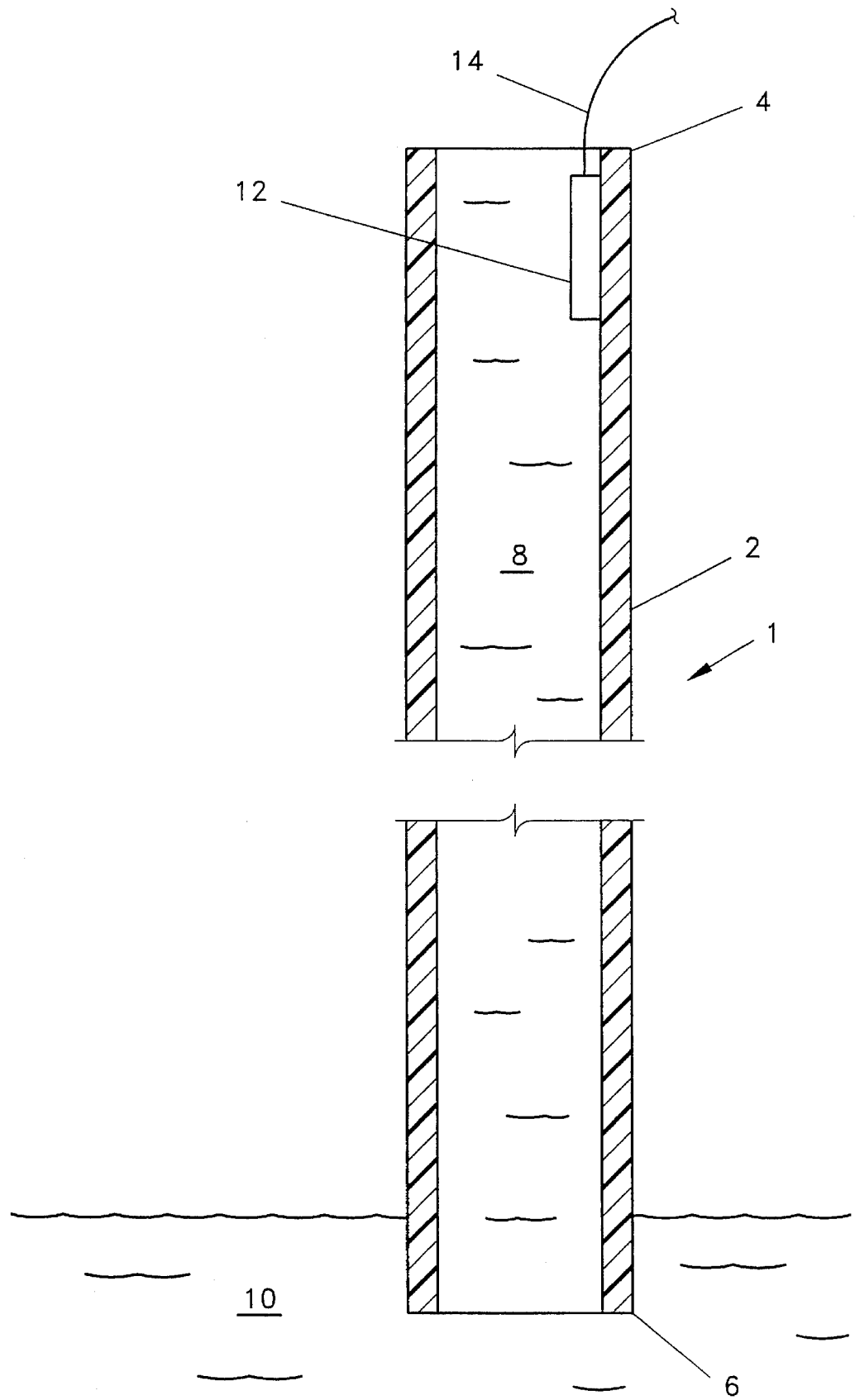
FIG. 1 is a sectional view of an intermingling capillary half-cell.

An embodiment of an intermingling capillary 0 reference half-cell (1) is shown in FIG. 1. The main component of the reference half-cell (1) is a capillary tube (2) having a first end (4) and a second end (6). Reference fluid (8) may be introduced into the capillary tube (2) by injecting the reference solution liquid (8) under positive pressure into one end or by drawing reference solution liquid (8) under negative pressure. The first end (4), is closed after receipt of the reference solution liquid (8), while the second end (6)

remains open. In use, at least the second end (6) is immersed in a test solution liquid (10) whereby the reference solution liquid (8) is in direct open contact with the test solution liquid (10) while the reference solution liquid (8) substantially remains within the capillary tube (2).

The second component of the reference half-cell (1) is an electrode element (12) placed near the first end (4) of the capillary tube (2) and in contact with reference solution liquid (8). A wire (14) provides electrical contact between the electrode element (12) and a voltmeter (not shown).

The use of a capillary tube (2) having a closed end (4), and filled with substantially incompressible reference solution liquid (8) constrains the reference solution liquid (8) from free flow volume discharge under the influence of atmospheric pressure or hydraulic pressure of the test solution liquid (10). Therefore, the reference solution liquid (8) remains within the capillary tube (2) and remains pure except as it is diluted by either diffusion between the reference solution liquid (8) and the test solution liquid (10) at the second end (6), or by flow induced by thermal expansion or contraction of the capillary tube (2) when the coefficient of thermal expansion of the capillary tube (2) is different from the coefficient of thermal expansion of the reference solution liquid (8), and the reference half-cell is at a temperature different from the test solution liquid (10) into which it is immersed. Therefore, the reference electrode element (12) "sees" pure reference solution liquid (8) until test solution liquid (10) is drawn by diffusion or thermally induced flow near the electrode element (12). The amount of time that the reference solution liquid (8) remains pure depends on the concentration differences of the chemical species in the liquids and depends on the distance between the second end (6) of the capillary tube (2) and the electrode element (12). Hence, the time in service of the present invention depends upon the length of the capillary tube. The capillary tube (2) may be of any material chemically compatible with the reference solution liquid (8) and the test solution liquid (10). The preferred material is plastic for ease of construction and handling including coiling the capillary tube (2). It is preferred that the open end (6) of the capillary tube (2) is turned upward to avoid the possibility of trapping an air bubble in the open end (6) and open circuiting the reference half-cell (1).

Figure 2:
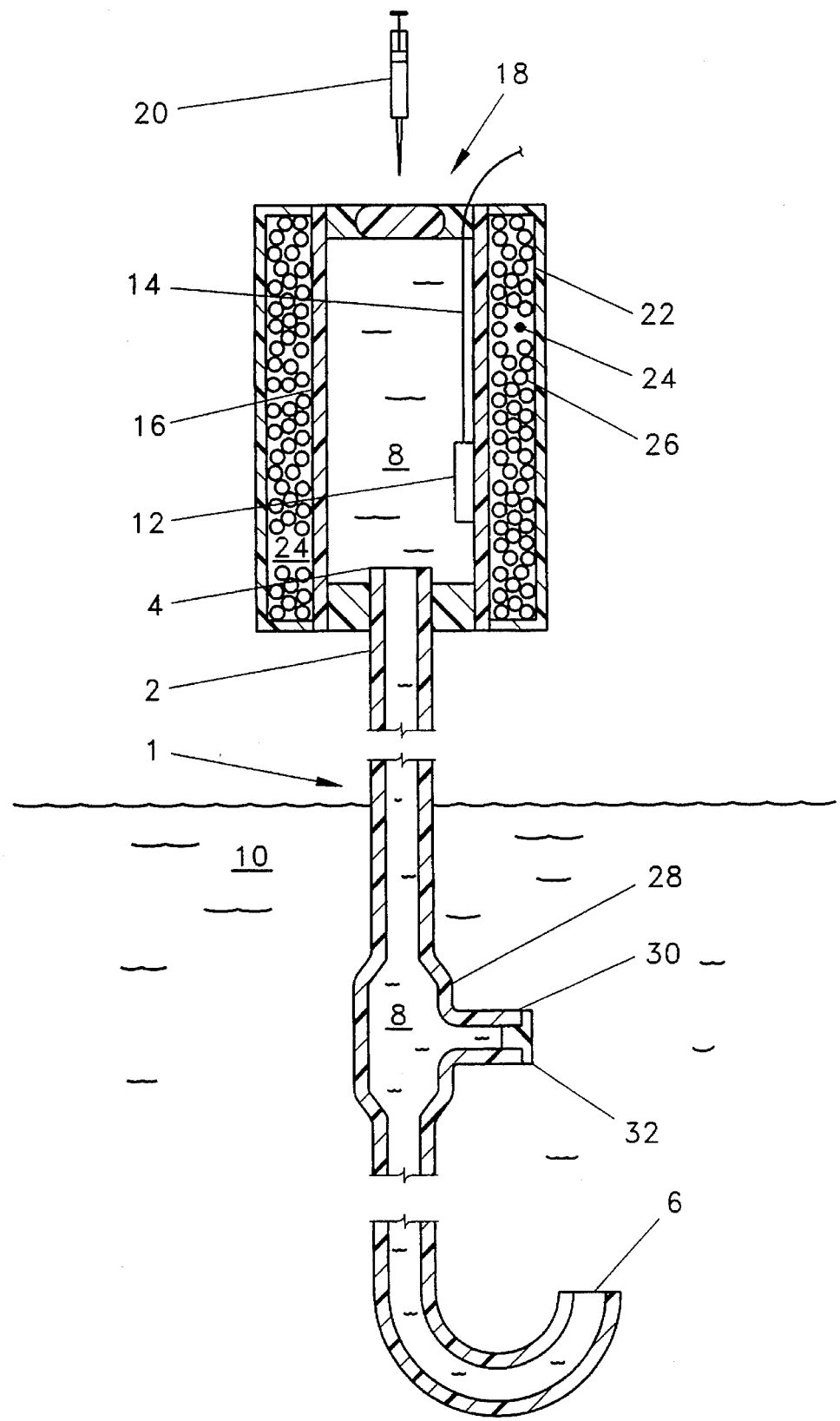
FIG. 2 is a sectional view of an intermingling capillary half-cell with a reference fluid reservoir.

A second embodiment is shown in FIG. 2 wherein a reference fluid reservoir (16) is sealably attached to the capillary tube (2) near the first end (4). The reference solution liquid reservoir may have a septum (18) for admitting reference solution liquid (8) with a syringe (20). The reservoir may be deformable like a squeeze bulb or plunger, or attached to a squeeze bulb for drawing reference solution liquid into the reservoir (16) and capillary tube (2). Reference solution liquid (8) may be admitted by any of several means including but not limited to (1) submersion, (2) osmosis across a semi-permeable membrane, (3) vacuum pump or vacuum bottle and valve arrangement, and (4) positive pressure pump and valve arrangement.

Additional features may be added for convenience of operation. An outer housing (22) may be placed around a portion of the reference half-cell (1) creating an annular space (24) that may be filled with material (26) having a density greater than that of water as an aid to submerging the reference half-cell (1).

An enlarged section (28) may be added to provide increased volume between the open end (6) of the capillary tube (2) and the electrode element (12). The increased volume mitigates thermally induced flow of the reference solution (8). The enlarged section may be deformable for admitting or expelling liquid from the capillary.

A port (30) and cap (32) may be provided separately or in combination with the enlarged section (28) for filling the capillary tube (2) with reference solution liquid (8). The port (30) may be any tee or fluid tight attachment but is preferably a female hypodermic needle fitting and the cap (32) may be any closure that is sealably compatible with the port (30) but is preferably a male hypodermic needle fitting.

Either embodiment shown in FIGS. 1 or 2 may be used as a double junction reference half-cell. A double junction may be made by immersing the second end (6) of the capillary in a non-interfering salt solution liquid then drawing sufficient salt solution liquid into the capillary tube to displace about half of the reference solution liquid. Alternatively, the port (30) may be used to introduce a non-interfering solution liquid in a portion of the capillary tube (2) between the port (30) and the open end (6) of the capillary tube (2) for making a double junction half-cell. The electric potential provided by this reference half-cell is stable until diffusion causes the reference solution liquid (8) near the electrode (12) to be diluted by either the non-interfering solution liquid or the test solution.

Various combinations of reference solution liquid (8) and electrode element (12) may be used. Examples include but are not limited to (i) a reference solution liquid (8) of 4 molar potassium chloride saturated with silver chloride in combination with an electrode element (12) of silver chloride electrolytically deposited on silver, and (ii) a reference solution liquid (8) of saturated calomel with an electrode element (12) of calomel electrolytically deposited on silver.

Figure 2A:
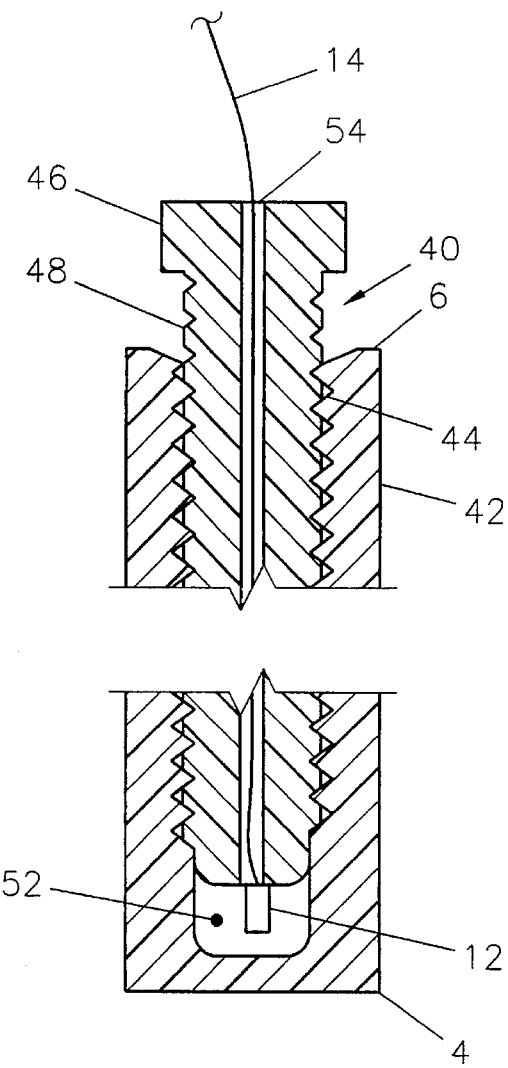
FIG. 2a is a cross section of a further embodiment of an intermingling capillary half-cell.
Figure 2B:
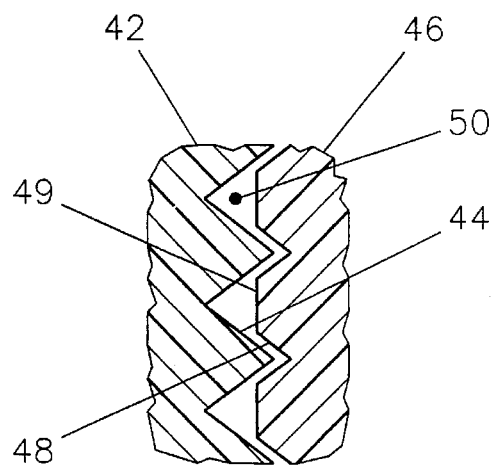
FIG. 2b is a cross section of modified threads.

Further, as shown in FIG. 2a, the capillary may be formed by modifying a screw type thread (40) thereby providing a helical capillary. An outer housing (42), having a first end (4) that is closed and a second end (6) that is open, is provided having internal threads (44). A rod (46) having outer threads (48) is threadably engaged into outer housing (42). With reference to FIG. 2b, one sees that the outer threads (48) have been modified to have a helical flat surface (49) thereby creating a helical capillary opening (50) between the outer threads (48) and the internal threads (44). The rod (46) permits passage of wire (14) to the reference electrode element (12), preferably via a hole (54). The hole (54) is preferably sealed with a sealing compound.

Figure 2C:
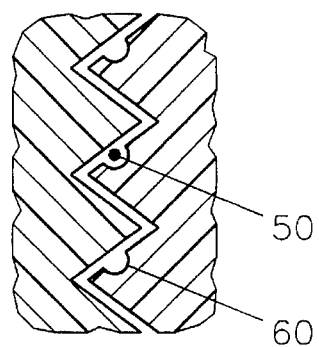
FIG. 2c is a cross section of a further modification of threads.
Figure 2D:
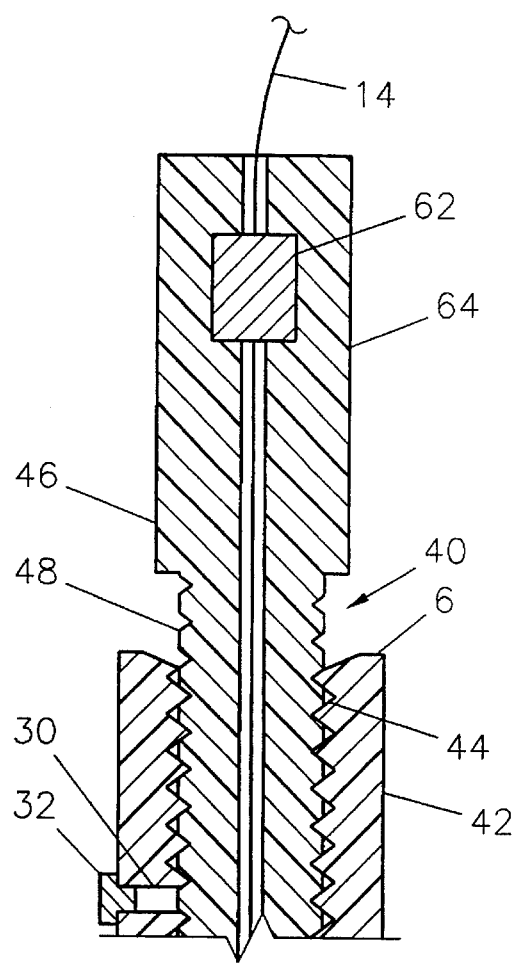
FIG. 2d is an intermingling capillary half-cell with a signal conditioning circuit.
Figure 2D:
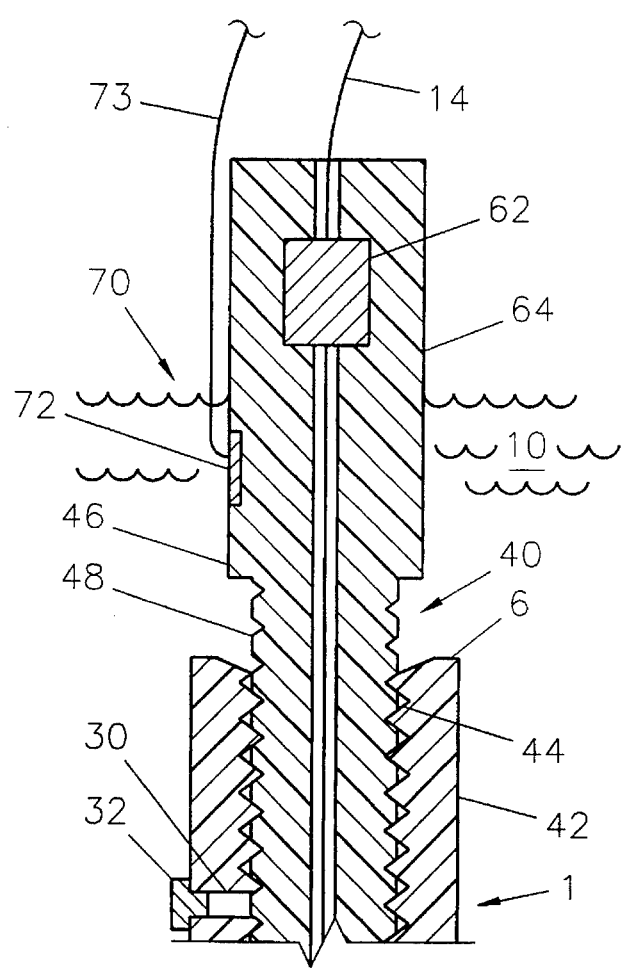
Figure 2D:
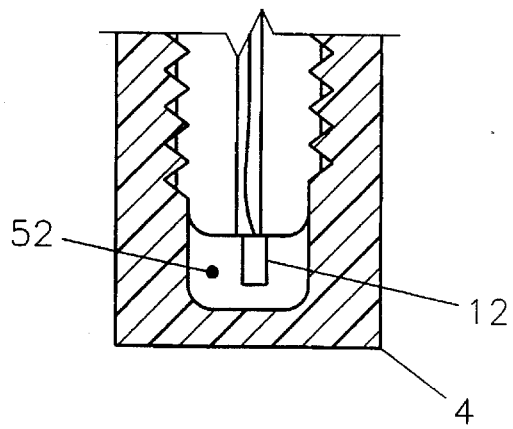

Reference solution liquid is placed within the outer housing (42) and the rod (46) threadably engaged thereby obtaining reference solution liquid in a reservoir volume (52) and in the helical capillary (50). The reference electrode element (12) is positioned within the reservoir volume (52) near the first end (4). This embodiment may be modified by addition of a port (30) and a sealable cap (32) to provide a double junction half-cell reference electrode as illustrated in FIG. 2d.

It will be apparent that many modifications are possible wherein the capillary is formed by other mechanical interfaces between mating parts. For example, the inner thread (44) may be modified in addition to or instead of the outer thread (48). The thread may be modified in other ways as illustrated in FIG. 2c wherein the helical capillary (50) is defined by a helical groove (60).

A yet further embodiment is the use of a syringe wherein the outer housing is not threaded but an inner slidable syringe plunger has a helical groove thereon forming a capillary between the helical groove and the smooth wall of the outer housing.

It is further recognized that the invention is not limited to circular cross section geometry. A slidable syringe plunger may be of any cross section. A threadably engaged capillary may be of any cross section provided the outer housing may be split and re-sealable.

It will be further appreciated that, while convenient, the invention is not limited to helical shaped capillary. A serpentine groove on a flat surface placed adjacent to a second flat surface defines a capillary operable according to the present invention.

There are several advantages of a capillary formed by mechanical interface of mating parts including ease of cleaning the walls of the capillary. The threaded rod and housing is especially advantageous because handling a long capillary tube is avoided.

It will be appreciated by those skilled in the art of electrochemical cells that the cells typically have high internal electrical resistance thereby yielding a high impedance or "weak" electrical signal. There are many ways to measure weak electrical signals, and it is generally recognized that a high impedance meter, eg. voltmeter, is needed.

Even with a high impedance meter, there are applications wherein a weak signal is adversely affected. For example, when an analog signal is transmitted over a long distance, eg. 300 ft, the internal electrical resistance of the long wire and outside signals such as radio signals can interfere with the measurement signal. There are many ways of conditioning the signal to overcome these problems including but not limited to signal digitizing and signal amplification. In the present invention, the signal current is amplified with an operational amplifier voltage-follower circuit. The circuit may be included with the intermingling capillary electrochemical half-cell as shown in FIG. 2d. The circuit (62) is sealed within an housing extension (64) of the outer housing (42). Electrical power to the circuit may be provided by any means, and the electrical power source may be remote- or proximate to the intermingling capillary electrochemical half-cell. It is preferred that the electrical power source be remote from the half-cell, and near the meter. This arrangement, of course, requires two additional electrical leads between the intermingling capillary electrochemical half-cell and the meter. It will be appreciated by those skilled in the art of instrument signal conditioning that an advantage of an operational amplifier circuit is that its output signal is compatible with a wide variety of signal reporting instruments including but not limited to data loggers, strip chart recorders, and lower impedance voltmeters.

Figure 2E:
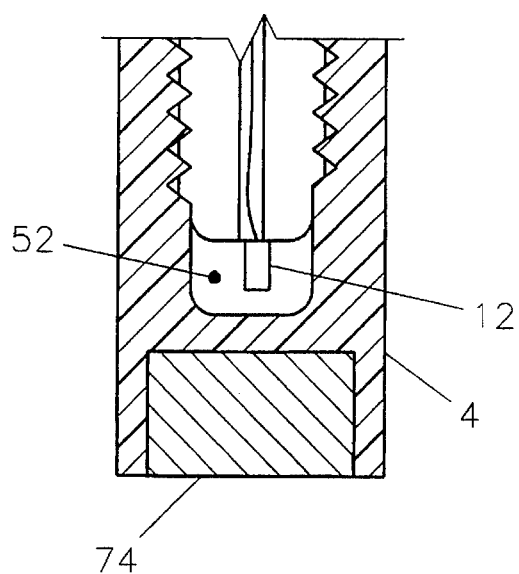
FIG. 2e is a combination electrode incorporating an intermingling capillary half-cell.

A yet further embodiment is shown in FIG. 2e. This embodiment is a "combination electrode" comprised of a sensing half-cell (70), intermingling capillary reference half-cell (1), and signal conditioning circuit (62). The sensing half-cell (70) comprises a sensing electrode (72) and wire (73) and a test solution liquid (10). The sensing electrode (72) may be any ion selective electrode, for example a bromide ion selective electrode that is silver having a coating of silver bromide. The sensing electrode (72) may be of any convenient shape and may be placed in any location on the combination electrode. The wire (73) may be placed internally or externally, but is preferably internal proximate to the wire (14).

For submersible applications, the combination electrode must sink. A weight (74) may be added wherein the weight has a density greater than the liquid, usually water, into which the combination electrode is submerged. The weight may be of any such material including but not limited to shot, and solid stainless steel.

EXAMPLE 1

An experiment was conducted using an intermingling capillary reference half-cell with a double junction constructed in accordance with the present specification and drawings. The purpose of the experiment was to measure the concentration of a bromide tracer test solution liquid using a first reference half-cell together with a second sensing half-cell of silver bromide on silver, with both half-cells connected to a voltmeter.

The intermingling reference half-cell utilizes a capillary tube of about 60 cm in length and having an internal diameter of about 0.03 cm. The capillary tube was first filled with a reference solution liquid of 4 molar potassium chloride saturated with silver chloride by injecting the reference solution liquid through the septum with a hypodermic needle and syringe. Next, a non-interfering solution liquid of 10 percent potassium nitrate was added through the port into the lower half of the capillary tube, thereby establishing the reference solution/non-interfering solution liquid interface within the enlarged section of the capillary tube. An electrode element of silver chloride on silver was placed within the reference solution liquid reservoir with a surface of the electrode element in contact with the reference solution liquid. The non-interfering solution liquid is needed to prevent the chloride of the reference solution liquid from entering the test solution liquid, to prevent any reaction between the bromide of the test solution and the silver of the reference solution liquid.

A 4 liter graduated cylinder was filled with tap water and stirred for about a day to insure a constant temperature and composition throughout the volume of water. Water temperature stabilized at about 23° C. Water analysis showed that the water contained calcium bicarbonate and calcium sulfate and had an ionic strength of about 0.0044 molar. The reference and sensing half-cells were immersed into the water and allowed to stabilize for about 2½ hours.

Potassium bromide was added to the water over a 3 hour period in increments so that the bromide concentration ranged from 0.17 to 50.0 milligrams per liter. For each increment, the activity coefficient and the activity of the bromide were calculated based upon the ionic strength of the water and the additional ionic strength of the potassium bromide according to Nernst-Peters equation provided in Garrels, R. M., and Christ, C. L., *Solutions, Minerals, and Equilibria,* Harper & Row, NY, 1965.

Figure 3:
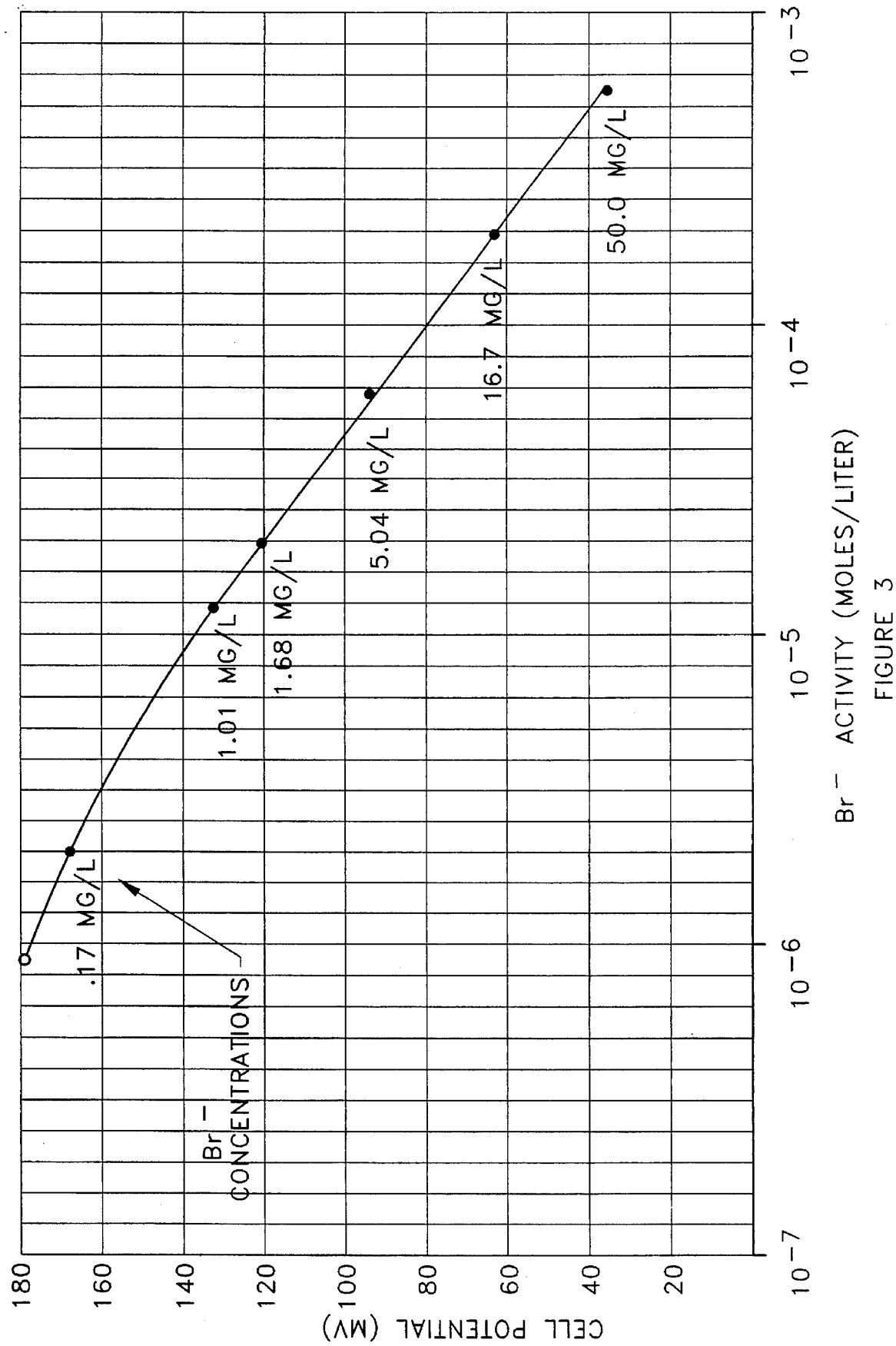
FIG. 3 is a plot of voltage potential versus analyte activity for the experiment of Example 1.

Results are shown in FIG. 3. The electropotential as measured in millivolts is linear with the logarithm of activity of the bromide for bromide concentrations between 1 and 50 milligrams per liter. The non-linearity at very low activities is characteristic of ion-selective half-cells. In this experiment, the non-linearity is caused by the slight solubility of the silver bromide of the sensing half-cell electrode. The upper left data point (40) is the electropotential of the water before addition of potassium bromide plotted against the activity of bromide calculated from the solubility product of silver bromide as listed in the Handbook of Chemistry, N. H. Lange, Handbook Publishers, Inc., Sandusky, Ohio, 1956.

The graduated cylinder was then covered to prevent evaporation and stirring maintained for about 19 hours. Total drift of the electropotential readings was −3.7 millivolt representing an apparent 16 percent increase of bromide activity. The electrochemical potential was then stable at 31.6 millivolts. At about the 20th hour, 0.32 grams of sodium sulfite powder was added to the water. The electropotential increased by 4 millivolts, but within 2 hours stabilized at 33.6 millivolts, which was the expected value after the salt addition.

During the two hours after the salt addition, electropotential drift was −3.5 millivolts. During the next 66 hours (total elapsed time about 116 hours), total drift was about −0.5 millivolts.

At about the 117th hour, sodium sulfide was added in two increments to test the response of the second sensing electrode to a sulfide chemical interference. The first addition was 0.066 milligrams per liter and the second was 0.325 milligrams per liter. The electropotential difference between these two increments was 2.1 millivolts. Analysis using the Nernst-Peters equation (Garrels and Christ, 1965) shows that the response of the sensing half-cell to sulfide was 5 percent of the theoretical Nernst slope. It was observed that the bromide electrode was visibly darkened by a coating of silver sulfide on the silver bromide.

Two hours later (at about the 119th hour), the bromide concentration was increased from 50 to 82 milligrams per liter and the bromide activity calculated. The measured change in electropotential due to bromide addition was 11.9 millivolts, which is again 95 percent of the theoretical Nernst slope. Hence, the change in electropotential due to an increase in bromide concentration was unaffected by either the silver sulfide on the bromide electrode or the bisulfide in the test solution liquid.

For the next 18 days, (total elapsed time of about 23 days) the electrodes and test solution liquid were undisturbed, and total drift of electropotential was −0.4 millivolts.

At about the 23rd day, 10 milliliters of potassium bromide were added to the test solution liquid. Analysis showed that the electropotential response was still 95 percent of the theoretical Nernst slope. The electrodes and test solution liquid were left undisturbed for an additional 6 days during which time the total electropotential drift was −0.2 millivolt.

Over the total elapsed time of about 29 days, both the first reference half-cell and the second sensing half-cell demonstrated reliable stability with very little drift. The only significant undesirable drift in electropotential occurred during the first day of the experiment. The magnitude of this undesirable drift is typical of electrodes that are put into service after having been stored in a dry condition.

EXAMPLE 2

A second experiment using the present invention was carried out under field conditions in a water well using a first non-flowing capillary reference half-cell With a double junction, together with a second sensing half-cell in accordance with Example 1.

Two 100 foot lengths of insulated electrical wire were connected to both half-cells and the connections were made water proof with a commercial sealant. The opposite ends of the wires were connected to a high impedance voltmeter. The half-cells were immersed in water for about 17 hours prior to the experiment. The purpose of the immersion was to avoid excessive initial electropotential drift upon immersion of the half-cells into the well water.

After 17 hours, the half-cells were calibrated using solution liquids of natural ground water from the test well with known concentrations of reagent grade lithium bromide. Results of calibration showed that a 10 mg/L bromide solution liquid yielded a voltmeter reading of 62.1 millivolts, and that the bromide-sensing half-cell was responding at 56.2 millivolts per decade of decreasing bromide concentration, which is 95 percent of the theoretical Nernst slope.

Bromide was distributed within the vertical water column of the well as evenly as practical, and based on depth and diameter of the well, the initial average concentration of bromide was expected to be 202 mg/L. The half-cells assembly was lowered into the well and initial readings were taken at twelve 3 foot intervals along the vertical water column. Subsequent sets of readings were taken periodically.

Figure 4A:
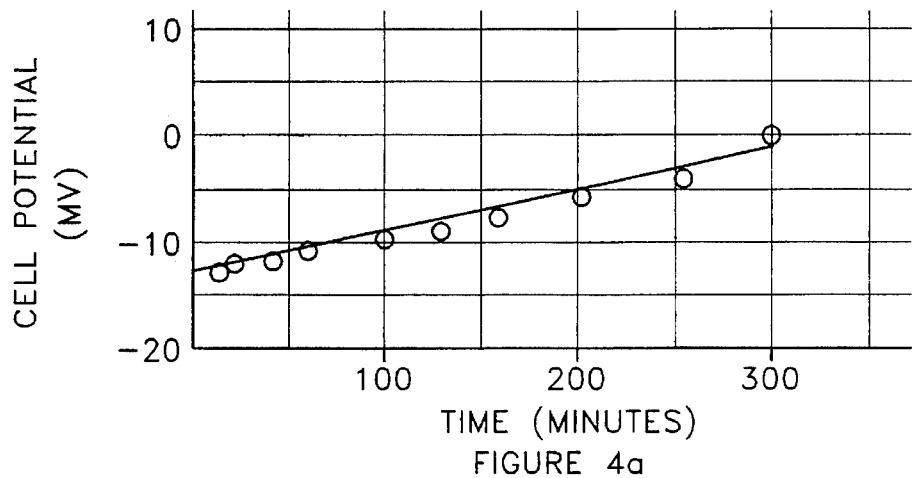
FIG. 4a is a plot of cell potential versus time at a depth of 1.5 feet for the experiment of Example 2.
Figure 4B:
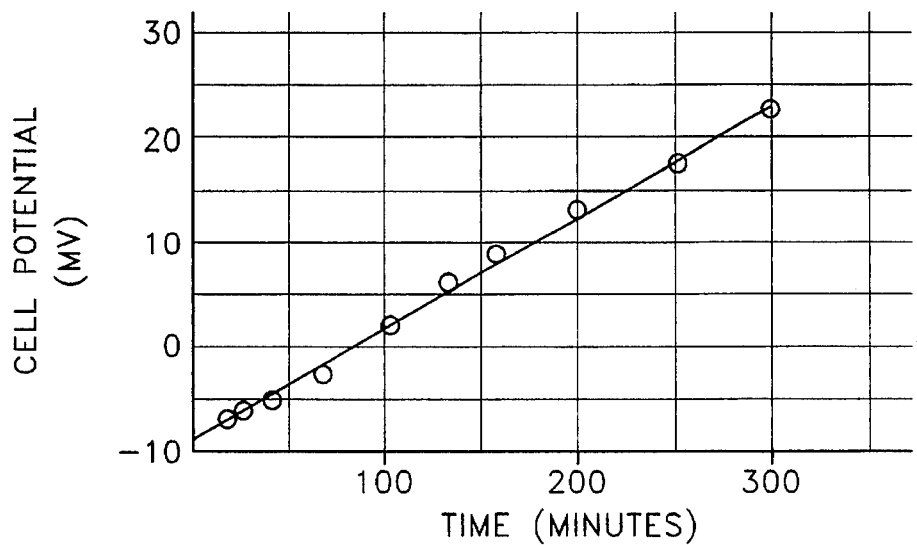
FIG. 4b is a plot of cell potential versus time at a depth of 19.5 feet for the experiment of Example 2.
Figure 4C:
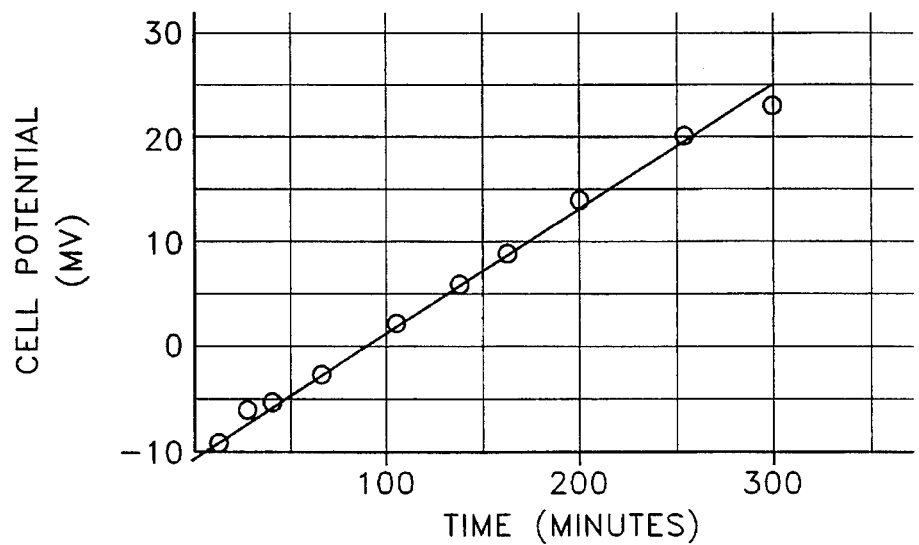
FIG. 4c is a plot of cell potential versus time at a depth of 31.5 feet for the experiment of Example 2.

It was expected that the bromide concentration would decrease with subsequent sets of readings as water in the well was refreshed by the groundwater, resulting in an increase in the voltage potential of the half-cells. It was further expected that the millivolt readings corresponding to the logarithm of the bromide activity would increase linearly with time. Indeed, as illustrated in FIGS. 4a, 4b, and 4c, graphs of millivolt readings with time for depths of 1.5 feet, 19.5 feet, and 31.5 feet respectively are increasingly linear within experimental error.

Extrapolation to time t=0.0 minutes, results in initial bromide concentrations at various depths ranging from 186 mg/L to 248 mg/L as given in Table 1. The initial bromide concentrations in. Table 1 represent a 3 foot vertical segment of the well except for the deepest interval which represents a 4 foot segment. A weighted average of the initial bromide concentrations of Table 1 yields an estimate of 206 mg/L, which is very close to the expected value of 202 mg/L.

TABLE 1

| Initial Bromide Concentrations |
| --- |
| Bromide concentration (mg/L) Depth at time = 0.0 |
| 1.5 219 |
| 4.5 202 |
| 7.5 194 |
| 10.5 186 |
| 13.5 194 |
| 16.5 186 |
| 19.5 186 |
| 22.5 179 |
| 25.5 194 |
| 28.5 194 |
| 31.5 202 |
| 34.5 248 |

The close agreement of the measured and expected initial bromide concentrations, together with the linear nature of the graphs demonstrate accurate and stable performance of the half-cells. Further, the half-cells were unaffected by the variation in hydraulic pressure between 1.5 and 34.5 feet of water.

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

I claim:

1. A capillary reference half-cell for immersion into a test solution liquid, comprising:

(a) a capillary having a length further having a portion of an amount of reference solution liquid therewithin, (b) said capillary constraining said portion of reference solution liquid from free flow volume discharge and said capillary having a first and second end, said first end further having a closure, said second end open, thereby forming at least one liquid junction between said reference solution liquid and said test solution liquid, and permitting diffusion between said reference solution liquid and said test solution liquid, and (c) an electrode element placed in contact with said reference solution liquid nearer said first end than to said second end wherein a voltage potential is related to a chemical concentration of said reference solution liquid, said voltage potential is constant while diffusion occurs until the diffusion dilutes said reference solution liquid near said electrode element so that a time in service depends upon the length of the capillary.

2. A reference half-cell as recited in claim 1, wherein said reference solution liquid is potassium chloride saturated with silver chloride and said electrode element is silver chloride on silver.

3. A reference half-cell as recited in claim 1, wherein said reference solution liquid is saturated calomel and said electrode element is calomel on silver.

4. A reference half-cell as recited in claim 1, wherein a deformable fluid reservoir is placed on said first end for use in admitting reference solution liquid into said capillary.

5. A reference half-cell as recited in claim 1, wherein said closure includes a fluid reservoir having a septum, said reservoir placed on said first end for admitting reference solution liquid into said capillary.

6. A reference half-cell as recited in claim 5, wherein said electrode is mounted in said fluid reservoir.

7. A reference half-cell as recited in claim 1, wherein said closure includes a fluid reservoir having a septum, said reservoir placed on said first end for use with a syringe for admitting reference solution fluid into said capillary.

8. A reference half-cell as recited in claim 7, wherein said electrode is mounted in said reservoir.

9. A reference half-cell as recited in claim 1, wherein said capillary is a tube and further comprises:

an enlarged section between said first end and said second end providing increased volume of said reference solution liquid.

10. A reference half-cell as recited in claim 1, wherein said capillary is a tube.

11. A reference half-cell as recited in claim 1, wherein said capillary is formed by a mechanical interface between mating parts.

12. A reference half-cell as recited in claim 11, wherein said mating parts are a housing threadably engaged with a rod.

13. A reference half-cell as recited in claim 12, further comprising a signal conditioning circuit mounted in a housing extension.

14. A combination electrode, comprising:

(a) a capillary having a length further having a portion of an amount of reference solution liquid therewithin;

(b) said capillary constraining said portion of said reference solution liquid from free flow volume discharge and said capillary having a first and second end, said first end further having a closure, said second end open, thereby forming at least one liquid junction between said reference solution liquid and said test solution liquid, and permitting diffusion between said reference solution liquid and said test solution liquid;

(c) an electrode element placed in contact with said reference solution liquid nearer said first end than to said second end wherein a voltage potential is related to a chemical concentration of said reference solution liquid, said voltage potential is constant while diffusion occurs until the diffusion dilutes said reference solution liquid near said electrode element so that time in service depends upon the length of the capillary; and (d) a sensing electrode mounted exterior to said capillary and in contact with said test solution liquid, thereby forming a sensing half-cell.

15. A combination electrode as recited in claim 14, further comprising a signal conditioning circuit mounted in a housing extension.

16. A method of using a capillary reference half-cell, comprising the steps of:

(a) filling a capillary with a portion of a reference solution liquid, said capillary having a first and second end, said first end closed, said second end open, (b) placing an electrode nearer said first end than to said second end and in contact with said reference solution liquid, (c) inserting said second end into a test solution liquid together with a second sensing half-cell for obtaining electrochemical measurements, and (d) preventing free flow volume discharge of said reference solution liquid into said test solution liquid.

17. A method as recited in claim 16, further comprising:

displacing an amount of said reference solution liquid with non-interfering liquid solution between from said second end to a length of said capillary and forming a double junction reference half-cell.

18. The method as recited in claim 16 wherein said capillary is initially filled with a first reference solution liquid, then a second non-interfering liquid solution is drawn into the second end with an interface between said first and second solutions between said first and second ends of said capillary, for providing a double junction reference half-cell.

* * * * *

UNITED STATES PATENT AND TRADEMARK OFFICE
CERTIFICATE OF CORRECTION

PATENT NO.  : 5,490,916
DATED       : 02/13/96
INVENTORS   : SH Hall

It is certified that error appears in the above-identified patent and that said Letters Patent is hereby corrected as shown below:

In column 1, after line 6, please insert

--This application is a continuation-in-part of 07/939,962 filed 09/04/92, now abandoned, which is a continuation of 07/810,995 filed 12/20/91, now abandoned.--

In column 4, line 59, please delete --0--.

Signed and Sealed this

Twenty-fifth Day of June, 1996

BRUCE LEHMAN

Attest:

Attesting Officer

Commissioner of Patents and Trademarks